United States Patent
Collier

(10) Patent No.: US 7,025,792 B2
(45) Date of Patent: Apr. 11, 2006

(54) VACUUM-ASSISTED PROSTHETIC DEVICE

(76) Inventor: Milo S. Collier, P.O. Box 909, Longview, WA (US) 98632

( * ) Notice: Subject to any disclaimer, the term of this patent is extended or adjusted under 35 U.S.C. 154(b) by 0 days.

(21) Appl. No.: 10/974,007

(22) Filed: Oct. 25, 2004

(65) Prior Publication Data

US 2005/0143838 A1    Jun. 30, 2005

Related U.S. Application Data

(60) Provisional application No. 60/514,049, filed on Oct. 24, 2003.

(51) Int. Cl.
*A61F 2/60* (2006.01)
(52) U.S. Cl. ....................................................... 623/33
(58) Field of Classification Search ............ 623/27–56, 623/26, 57–58
See application file for complete search history.

(56) References Cited

U.S. PATENT DOCUMENTS

| | | | | |
|---|---|---|---|---|
| 5,800,570 | A * | 9/1998 | Collier ........................ | 623/55 |
| 6,287,345 | B1 * | 9/2001 | Slemker et al. ............... | 623/34 |
| 6,645,253 | B1 * | 11/2003 | Caspers ........................ | 623/26 |
| 2002/0091449 | A1 * | 7/2002 | Caspers et al. ............... | 623/34 |
| 2004/0064195 | A1 * | 4/2004 | Herr ............................. | 623/24 |

* cited by examiner

*Primary Examiner*—Alvin J. Stewart
(74) *Attorney, Agent, or Firm*—Kolisch Hartwell, P.C.

(57) ABSTRACT

A prosthetic device for attachment to a residual limb is provided that includes a socket-forming member configured to receive the residual limb, a first portion, and a second portion that is operatively connected to the first portion and rotationally movable relative to the first portion. The prosthetic device also includes a pump attached to the first portion that is adapted to draw a negative pressure within the socket-forming member upon rotational movement of the second portion relative to the first portion.

32 Claims, 5 Drawing Sheets

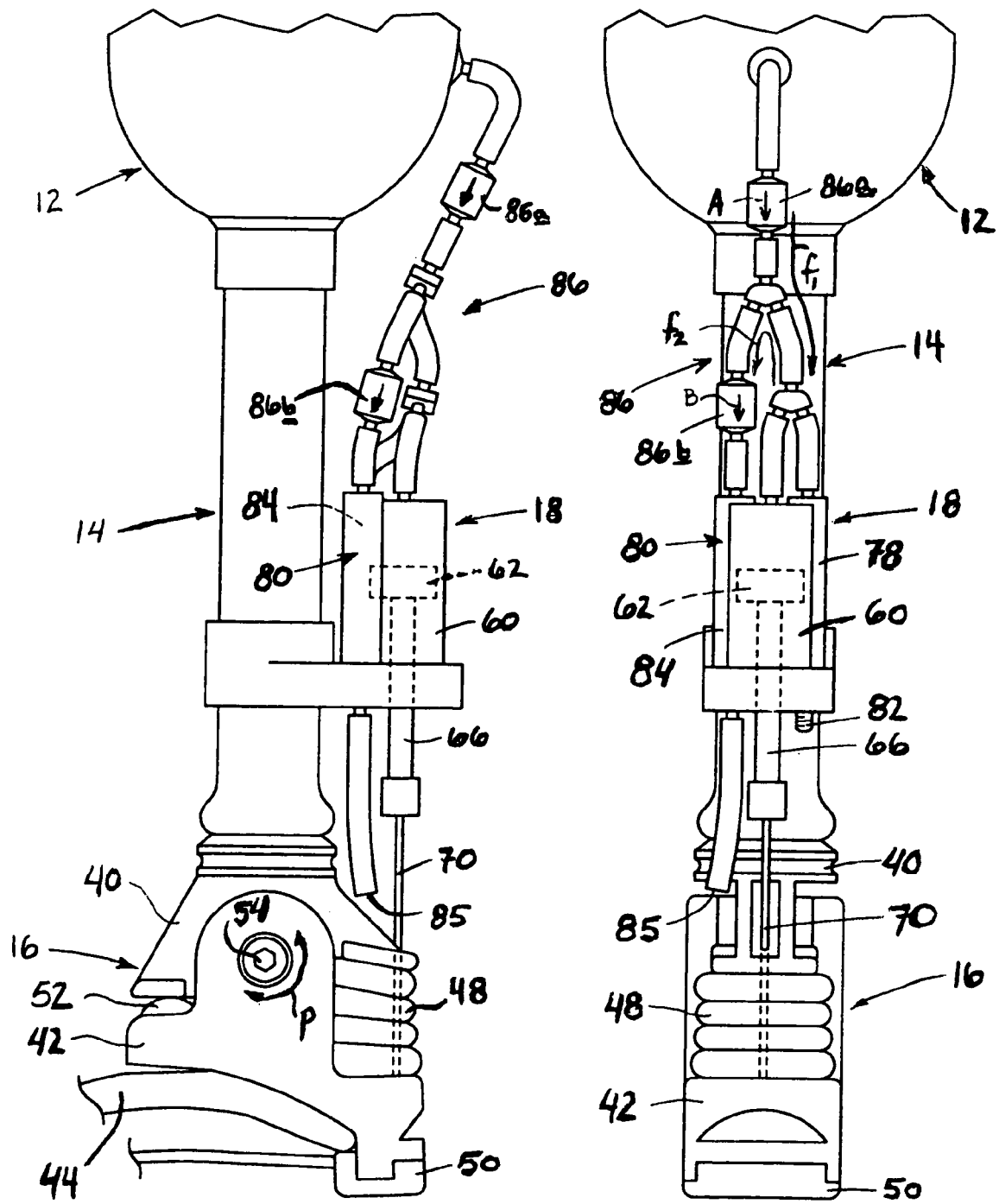

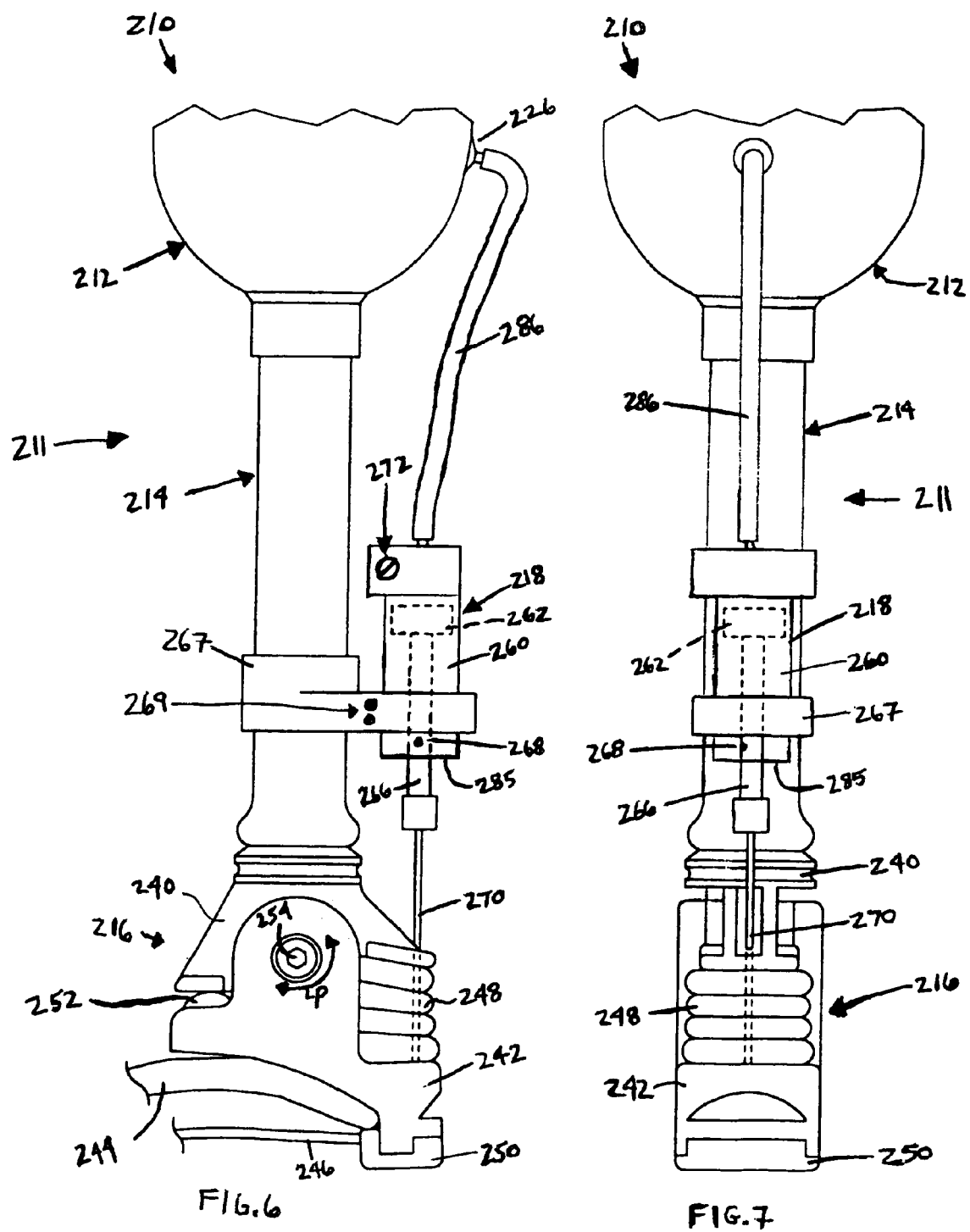

VACUUM-ASSISTED PROSTHETIC DEVICE

CROSS-REFERENCE TO RELATED APPLICATION

This application claims priority from U.S. Provisional Patent Application Ser. No. 60/514,049, filed Oct. 24, 2003 entitled VACUUM-ASSISTED PROSTHETIC DEVICE, the disclosure of which is incorporated herein by reference.

TECHNICAL FIELD

This disclosure relates generally to prosthetic devices, and more particularly to prosthetic devices which are attached to a residual limb with the assistance of vacuum pressure. The disclosed prosthesis includes a socket-forming member, and a structure attached to the socket-forming member that mechanically actuates a pump.

BACKGROUND

A prosthetic device, or prosthesis, is an artificial substitute for a part of the body such as a limb. Numerous prostheses have been developed to serve this purpose, each trying to replicate the function and appearance of the missing body part. Limb prostheses have been previously described in U.S. Pat. No. 5,545,234 to Collier Jr. and U.S. Pat. No. 5,800,570 to Collier, which are hereby incorporated by reference.

Most prosthetic devices have sockets that receive an amputee's residual limb. There are generally two categories of sockets: hard socket systems wherein the residual limb fits directly into the socket without any type of liner or sock, and soft socket systems which utilize a liner or insert. With either category of socket, the challenge is to keep the residual limb tightly confined within the socket so as to maintain the prosthetic device on the residual limb. The more active a prosthetic device user is, the more important it is to have the prosthetic device maintained in a tight association with the residual limb. Loss of a prosthetic device can cause a user to fall and suffer serious injury.

There are various methods of maintaining prosthetic devices on the residual limbs of users. Prosthetic devices may, for example, be suspended from a user's body by some form of pulley, belt or strap suspension. Such prosthetic devices may employ various harnesses and/or lacings. Sleeve suspensions also may be used. Such prosthetic devices may employ a constrictive rubber sleeve tube rolled over the top of their prosthetic device and onto the upper aspect of their residual limb. Such a sleeve suspension may be used in combination with other forms of suspension.

Other systems may employ electric or mechanical pumps that establish positive or negative pressure to maintain prosthetic devices on the residual limb of users. However, these systems typically look unnatural, are heavy, and are often difficult to use. Further, these systems may require pressures that are so forceful that there is a risk of damage to residual limb tissue, such as generalized trauma, vascular disruption, tissue atrophy, and sequential loss of tissue. For example, some systems utilize mechanical hand pumps to draw negative pressure from within the prosthetic device. These pumps typically are difficult to use, and require frequent pumping to counteract leakage of air into the prosthetic device. Other systems utilize an electrical motor-driven pumps to establish negative or positive pressure within the prosthetic device. These pumps typically are heavy, and require relatively high pressure to maintain the prosthetic device on the residual limb. Yet another system uses a weight-actuated mechanical pump to draw negative pressure within a lower limb prosthetic device. Such pump typically is attached to the prosthetic foot, and acts like a shock absorber. The pump is bulky, heavy and unnatural looking, and requires the user to apply downward pressure to actuate the pump.

There is a need to provide a lightweight prosthetic device that employs a mechanical pump to establish a negative pressure within the device for attachment to the residual limb of a user. Such a lightweight device would allow a user to attach the prosthetic device to the residual limb with lower negative pressures. There is also a need to provide a natural looking device that creates or maintains negative pressure during normal ambulatory motion by a user. Finally, there is a need to provide a device with a pump that may be adjusted to provide more or less draw based on the physical characteristics and activity level of the user.

BRIEF DESCRIPTION OF THE DRAWINGS

FIG. 2 is an enlarged side view of the lower extremity prosthetic device shown in FIG. 1.

FIG. 3 is a rear view of the lower extremity prosthetic device shown in FIG. 1.

FIG. 6 is a side view of a prosthetic device, according to yet another embodiment of the present invention.

FIG. 7 is a rear view of the prosthetic device shown in FIG. 6.

DETAILED DESCRIPTION OF THE DEPICTED EMBODIMENTS

Figure 1:
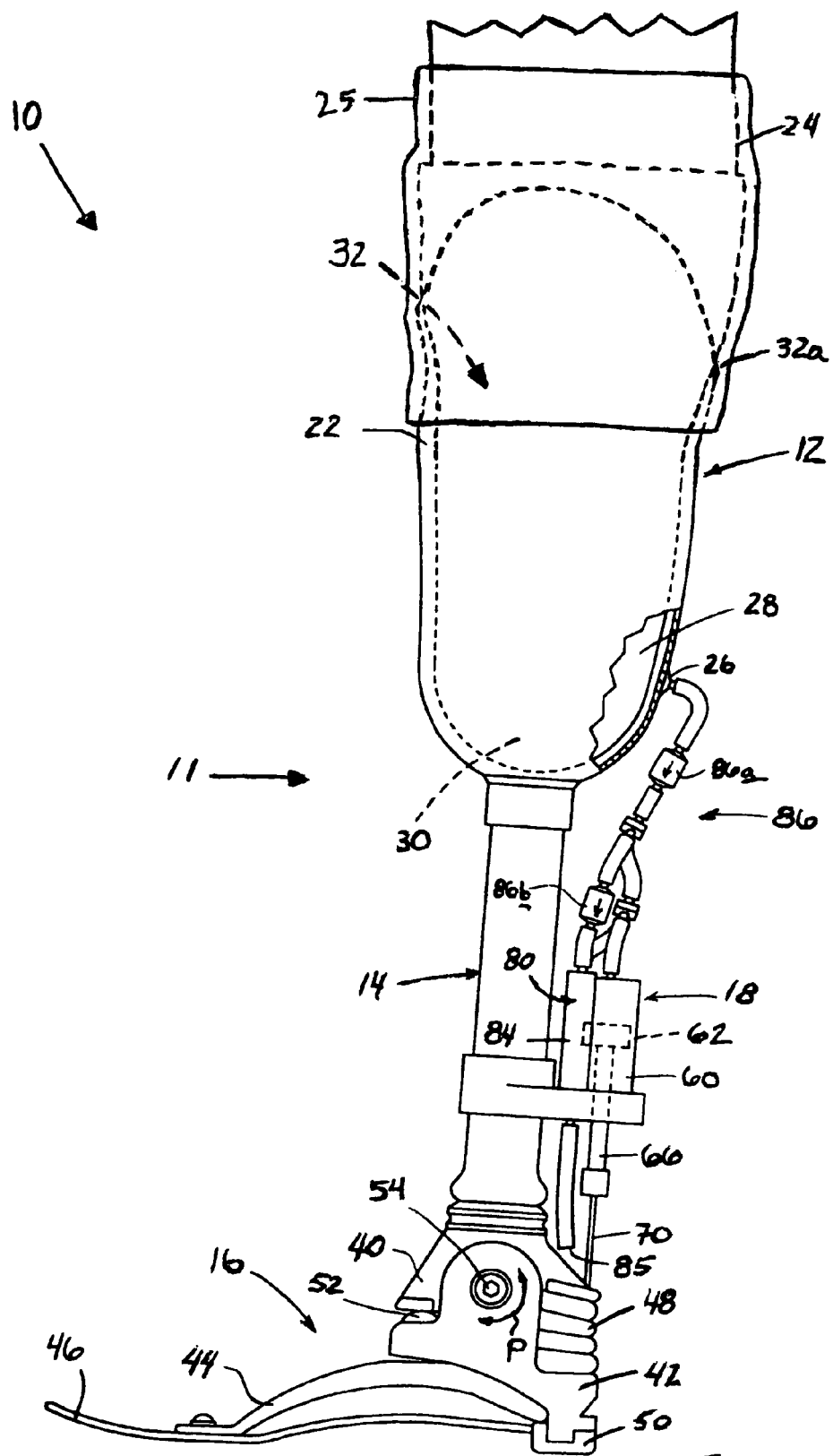
FIG. 1 is a side view of a prosthetic device constructed in accordance with an embodiment of the present invention, the prosthetic device being a lower extremity prosthetic device.

FIGS. 1–3 show a lower extremity prosthetic device suitable for use by an individual with a below the knee amputation. It will be appreciated, however, that the present invention need not be so limited. In FIG. 1, the prosthetic device is indicated generally at 10.

As shown, device 10 may include a leg member 11, a foot member 16, and a pump 18. The leg member 11 may include a socket-forming member 12, a shin member 14, and an upper ankle 40. Socket-forming member 12 may include a socket shell 22 formed from a rigid material, such as a hard plastic. Socket shell 22 may be configured with a socket cavity 32 adapted to maintain a substantial portion of a residual limb 24 in a stable manner while a user is standing or moving. Socket shell 22 also may be provided with a port 26, which may include a fitting configured to allow fluid to flow into or out of the socket shell. As will be appreciated upon reading further, port 26 may be adapted to draw fluid (e.g., air) from within the socket-forming member so as to create or maintain a negative pressure within socket cavity 32.

Referring still to FIG. 1, it will be noted that the user may place a liner 28 over his/her residual limb 24 prior to donning prosthetic device 10. Liner 28 may be made of a material impermeable to air or liquid, such as neoprene or nonporous polyurethane. However, in some embodiments the liner may be constructed with one or more layers of a material that is permeable to air and/or liquid such as cotton cloth. Liner 28 may be closed at a distal end 30, and thus may cover an end of residual limb 24, preventing direct contact of residual limb 24 with socket shell 22. Liner 28 thus may serve to provide protection of the residual limb tissue, and may assist in maintaining prosthetic device 10 on residual limb 24.

When socket shell 22 is placed over residual limb 24, which may be fitted with a liner 28, a substantially air-tight seal may be formed between socket shell 22 and liner 28 adjacent upper opening 32a. This, in turn, may restrict the flow of air into socket cavity 32 via upper opening 32a. A seal 25 may also be worn to cover the interface between socket shell 22 and liner 28, and between liner 28 and residual limb 24. Seal 25 may be made of a material impermeable to air or liquid, such as neoprene or nonporous polyurethane. Seal 25 may also restrict the flow of air into socket cavity 32. Accordingly, a negative pressure may be created or maintained within socket cavity 32 via port 26 of socket shell 22. It will be appreciated that negative pressure refers to a pressure lower than atmospheric pressure, which may be achieved by drawing fluid, such as air, from the socket cavity using a pump as described below.

Referring again to FIGS. 1–3, it will be noted that socket-forming member 12 may be supported by shin member 14 and upper ankle 40. The shin member may be in the form of a tube, with inner and outer diameters selected to achieve a desired strength and flexibility. The upper ankle may be fixed relative to the shin member, and the socket-forming member 12, and may be configured to form the distal end of leg member 11. The shin member and upper ankle may be constructed from a nylon polymer, from carbon graphite, or from some other material having enough structural integrity to support the weight of a user. Alternatively, the shin member and upper ankle may be constructed from aluminum or titanium in order to decrease the overall weight of prosthetic device 10. This weight will at least partially determine the amount of negative pressure needed to secure prosthetic device 10 to residual limb 24. Lighter prosthetic devices will require less negative pressure to secure the prosthetic device to the residual limb than heavier prosthetic devices. Typically, it is desirable to keep such negative pressure low in order to avoid damage to the residual limb.

A foot member 16 may be attached to leg member 11. In FIGS. 1–3, foot member 16 may include a lower ankle 42, a midfoot 44, and a toe plate 46. The lower ankle may also include a heel 50, above which a resilient element 48 may be mounted as shown. Another resilient element 52 may also be provided.

As will be appreciated, at least a first portion of the prosthetic device is rotationally movable relative to a second portion of the prosthetic device. For example, the first portion may be pivotally or flexibly rotatable relative to the second portion. Other modes of rotational movement may also be used to achieve similar results. In the embodiment shown in FIGS. 1–3, foot member 16 is pivotally movable relative to leg member 11. Specifically, lower ankle 42 is pivotally connected to upper ankle 40 by pivot member 54. The pivot member permits the foot member to be pivoted relative to the upper ankle, as indicated by arrow P. Because upper ankle 40 is substantially fixed relative to shin member 14 and socket-forming member 12, lower ankle 42 is also pivotal relative to the shin member and the socket-forming member.

Resilient elements 48 and 52 may work in combination to keep foot member 16 in a relatively neutral position when the structure is under minimal load, such as when the user is standing in place, or at rest. First resilient element 48 may urge the lower ankle to pivot clockwise relative to its position in FIG. 1. Second resilient element 52 may act oppositely, urging the lower ankle to pivot counterclockwise relative to its position in FIG. 1. The resilient elements thus cooperate to establish the neutral position shown in FIGS. 1–3. First and second resilient elements may be formed from any resilient material, such as a foam rubber, that provides yieldable resistance to pivot of lower ankle 42 relative to upper ankle 40 about pivot member 54.

Under normal walking operation, the user steps down on heel 50, thereby causing lower ankle 42 to pivot counterclockwise relative to upper ankle 40 away from the neutral position shown in FIGS. 1–3. During this counterclockwise pivot, lower ankle 42 may compress resilient element 48 against upper ankle 40, thereby creating an opposing force between resilient element 48 and the lower ankle. As the user continues forward, his or her center of gravity shifts from being over the heel, to being over the midfoot 44 and toe plate 46, thereby causing the lower ankle to pivot clockwise relative to the upper ankle. The initial clockwise rotation is assisted by the opposing force established between the lower ankle and resilient element 48 until the lower ankle and the resilient element both return to the neutral position shown in FIGS. 1–3. As the lower ankle continues to pivot clockwise relative to the upper ankle past the neutral position, the lower ankle may compress resilient element 52 against the upper ankle. This creates an opposing force between resilient element 52 and the lower ankle. The user completes his or her stride by lifting the heel from the ground and kicking off from the toe plate. The opposing force created between resilient element 50 and the lower ankle causes the lower ankle to pivot counterclockwise until the lower ankle and resilient element 50 return to the neutral position shown in FIGS. 1–3. This completes one iterative rotational movement of the lower ankle relative to the upper ankle.

As will be appreciated, a pump may be attached to a first portion of the prosthetic device, and may be adapted to draw a negative pressure within a socket-forming member upon rotational movement of a second portion of the prosthetic device relative to the first portion. The pump may include an actuator operatively configured relative to the second portion, such that the second portion acts on the actuator to effect drawing of the negative pressure by the pump upon rotational movement of the second portion relative to the first portion. For example, in the embodiment of FIGS. 1–3, pump 18 may be attached to leg member 11 above foot member 16. As will be discussed in more detail below, pump 18 further may include a tether 70 attached to the foot member. Upon ambulatory motion, the foot member will pivotally rotate relative to both the leg member and the pump. The foot member thereby acts upon the tether to actuate the pump, which draws negative pressure within the socket-forming member 12.

In the embodiment of FIGS. 1–3, pump 18 may include a pump cylinder 60 which carries a reciprocating piston 62. A piston arm 66 is attached to the piston and reciprocates with the piston. Although not particularly shown, the piston may be urged to a neutral position within the cylinder by a spring or other bias mechanism. As discussed below, this neutral position may be selected in order to maximize the amount of negative pressure drawn by the pump within the socket-forming member during each iterative reciprocating motion of the piston. The pump and pump components may be constructed from lightweight materials, such as aluminum, titanium or hard resins in order to maintain a low overall weight of prosthetic device 10. This weight will at least partially determine the amount of negative pressure needed to secure prosthetic device 10 to residual limb 24.

An actuator, such as a tether 70, may be secured to piston arm 66, threaded through an eyelet in resilient element 48 and fixed to foot member 16. The tether may be attached to heel 50 of lower ankle 42, or any other portion of the foot member. Tether 70 thus links piston 62 and piston arm 66 to the foot member such that the piston reciprocates as the lower ankle pivotally rotates relative to the upper ankle 40 during normal ambulatory motion of the user. As the lower ankle pivots counterclockwise, slack is provided to the tether and the biasing mechanism within the pump (not shown) causes the piston to reciprocate upwardly within the cylinder, thereby "charging" the pump. As the lower ankle pivots clockwise, the tether pulls downwardly on the piston arm and piston, thereby drawing negative pressure from within the socket-forming member 12, as discussed in more detail below. Thus, for each iterative rotational movement of the lower ankle relative to the upper ankle, the piston reciprocates once within the cylinder.

While the piston and piston arm may be formed from rigid materials such as lightweight metals or hard resins, tether 70 may be either rigid or flexible. For example, the tether may be formed from a cable, a strap, a cord, a wire, a string or a rod. Tether 70 may be secured to foot member 16 in any number of ways, including welding or by a screw or other fastening mechanism.

When foot member 16 is in a neutral position, as shown in FIGS. 1–3, piston 62 may also be positioned in a neutral position. FIGS. 1–3 illustrate the piston's neutral position to be approximately midway between a top and a bottom of cylinder 60. This neutral position of the piston within the cylinder may be adjustable so as to increase or decrease the amount of negative pressure drawn within the socket-forming member 12 with each stride of the user. In particular, for a fixed-length tether 70, the neutral position of the piston within the cylinder depends on the position of pump 18 relative to the foot member. A pump may be provided that is adjustably attached to leg member 11. Adjusting the attachment position of the pump with respect to the leg member would thereby also adjust the position of the pump with respect to the foot member. For example, raising the attachment position of the pump to the leg member would increase the distance of the pump from the foot member. Because of the fixed length of the tether, the neutral position of the piston within the cylinder would thus be lower. For each stride of the user, the pump could be charged a greater amount, and the pump would draw an increased amount of negative pressure for each iterative rotational movement of the foot member relative to the leg member. This may accommodate maximum pumping action for users with different length strides.

Pump 18 may further include an exhaust system 80, including a sweat efflux condensation chamber 84 and a discharge port 85. The condensation chamber may be replaced by, or supplemented with, tubing from which condensed liquid may flow out of pump 18 and away from prosthetic device 10.

A tubing system 86 may direct flow of fluid between socket-forming member 12 and pump 18, as well as provide directed flow of fluid between the various aspects of pump 18. To achieve this directed flow of fluids, tubing system 86 may be provided with a pair of one-way valves 86a, 86b. In the embodiment of FIGS. 1–3, valve 86a allows passage of fluid only in a direction A. Similarly, valve 86b allows passage of fluid only in a direction B.

As discussed above, negative pressure may be created within socket cavity 32 of socket-forming member 12 when piston 62 is displaced downwardly within cylinder 60. As foot member 16 pivots counterclockwise relative to leg member 11, the biasing mechanism (not shown) causes the piston to reciprocate upwardly within cylinder 60. Fluid within the cylinder may be vented via direction B through valve 86b and discharge port 85, thereby charging the pump. This flow of fluid is shown by flow path $f_2$. Due to one-way valve 86a, little or no fluid passes into the socket-forming member 12 as a result of the piston's upstroke.

As the foot member 16 pivots clockwise, tether 70 pulls piston arm 66 and piston 62 downward relative to cylinder 60. The downward reciprocating motion of the piston may draw fluid through valve 86a via direction A from substantially air-sealed socket cavity 32. This flow of fluid is shown by flow path $f_1$. Due to one-way valve 86b, little or no fluid passes into the cylinder through the exhaust system 80. Thus, downward reciprocating motion of the piston may create negative pressure within the socket-forming member 12.

It should be appreciated that once a negative pressure has been created within socket cavity 32, there may be some leakage of air into the socket cavity around seal 25 and upper opening 32a. The downward reciprocating motion of the piston provided during ambulatory motion may maintain the negative pressure within the socket cavity. It also should be appreciated that this flow of air through the socket cavity provides some ventilation to residual limb 24, thereby affording increased comfort to the user.

An additional benefit of providing negative pressure to the residual limb is that negative pressure within the socket cavity may help to counteract a loss of fluids within the residual limb otherwise caused by weight bearing pressure applied to the limb during use of the prosthetic device 10. In the absence of negative pressure, the constant weight bearing pressure applied to the limb during prosthetic use throughout the day may cause the residual limb to lose fluids and to decrease in size. This decrease in size may thereby cause discomfort to the user due to shearing forces between the residual limb and the socket-forming member. Application of negative pressure to the residual limb may function to limit the loss of fluid from the limb and the concomitant decrease in size of the limb.

Pump 18 may further include a regulator 78, which is best shown in FIG. 3. Regulator 78 may serve to regulate the negative pressure established by pump 18 within socket-forming member 12. The regulator may be integral with cylinder 60, or may be defined by a separate chamber such as that shown in FIGS. 1–3. The regulator may be configured to bleed negative pressure exceeding a predetermined maximum negative pressure. Regulator 78 may further be adjustable by manipulating a threaded screw 82 or other adjustment mechanism. A user, physician or health care professional thus may adjust the maximum negative pressure within socket-forming member 12 by adjusting the regulator to accommodate the particular needs of the user. The maximum negative pressure is selected: to ensure that the prosthetic device 10 is adequately secured onto the residual limb; to limit the loss of fluid from the residual limb caused by weight bearing pressures; and to prevent any detrimental physical effects to the user caused by excessive negative pressure, such as swelling of the limb and damage to the limb's tissues. This safe and effective maximum negative pressure may be determined based on the mass of the prosthetic device, as well as the physical condition of the user, and may be between 1–28 inches of mercury below ambient pressure.

Figure 4:
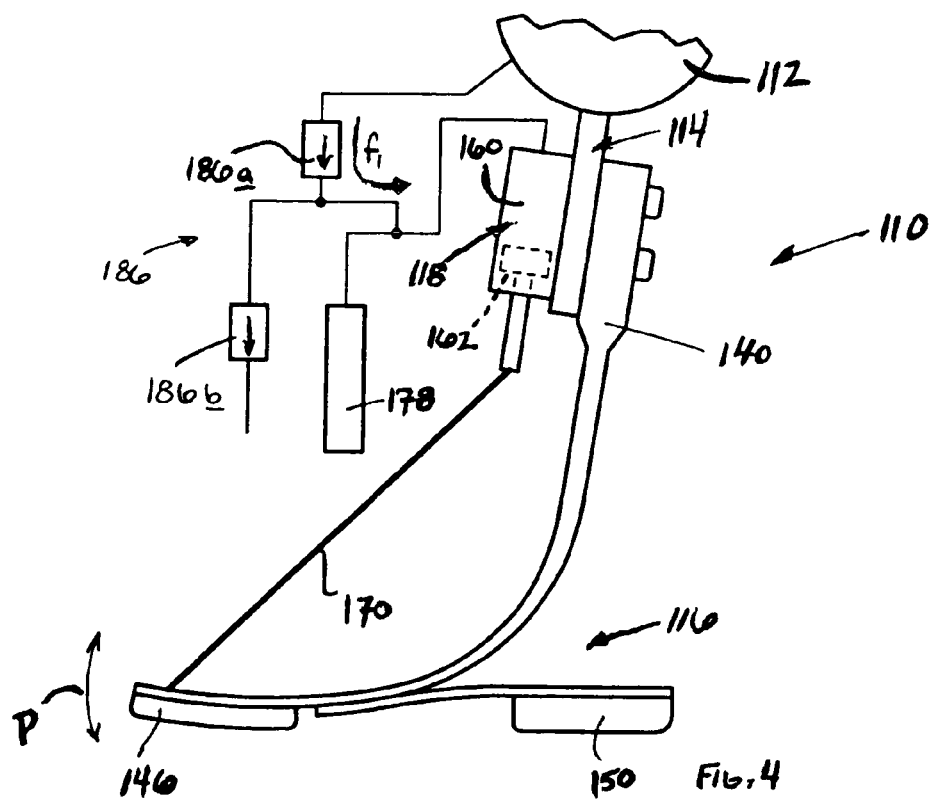
FIG. 4 is a side view of a prosthetic device, according to an alternative embodiment of the present invention, the prosthetic device being shown during a first phase of a walking motion.
Figure 5:
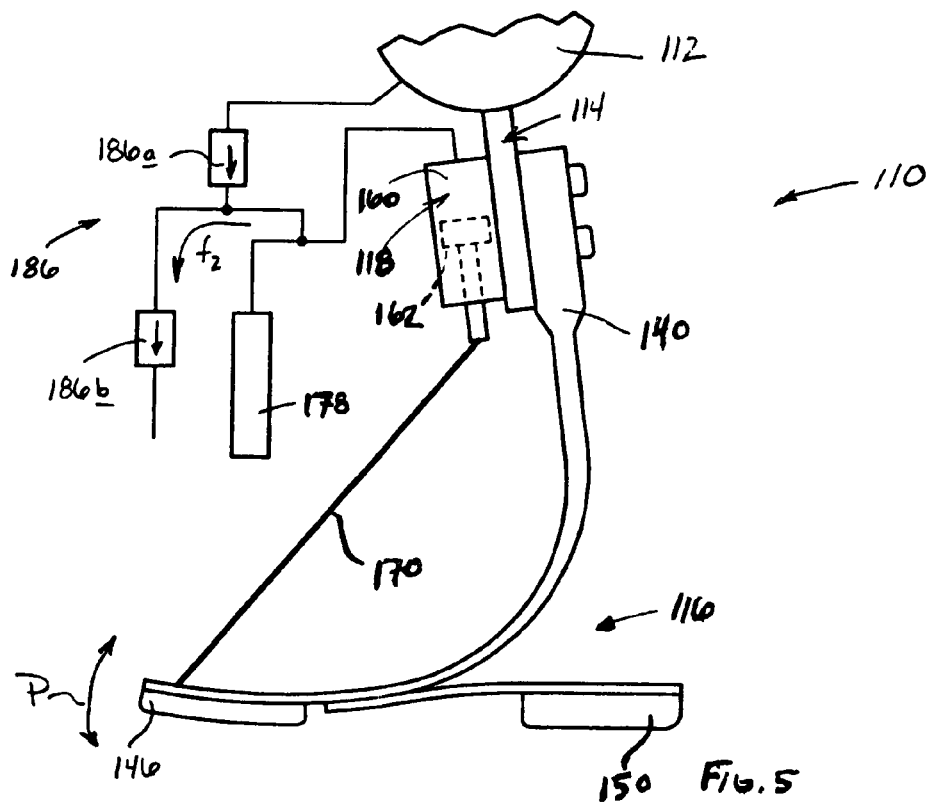
FIG. 5 is a side view of the prosthetic device of FIG. 4 during a second phase of a walking motion.

As further seen in a second embodiment prosthetic device shown at 110 in FIGS. 4 and 5, the displacement of piston 162 may be accomplished by rotational movement of virtually any two portions of a prosthetic structure. Such pivotal movement, however, typically will occur during functional movement of the prosthetic device. The prosthetic device depicted in FIGS. 4 and 5, for example, may include a structure in the form of flexible foot member 116, which includes a toe portion 146, and an ankle portion 140. As shown, ankle portion 140 may be connected to shin member 114, which in turn may be connected to socket-forming member 112. The socket-forming member may be configured to receive a residual limb as described above with respect to prosthetic device 10 of FIGS. 1–3.

A pump 118 may be provided for use in establishing a negative pressure in socket-forming member 112. The pump may include a pump chamber 160, and a piston 162 configured to reciprocate within the pump chamber. A bias element (not shown) may be provided to urge piston 162 upwardly within the pump chamber, such that the piston will return to a nominal at-rest position after downward reciprocating motion of the piston. A tether 170 may be connected to a piston arm of piston 162, and to toe portion 146 of flexible foot member 116.

When the pump chamber is fixed to shin 114, piston 162 may reciprocate within pump chamber 160 under normal ambulatory motion of a user of prosthetic device 110. This may create or maintain negative pressure within socket-forming member 112 through tubing system 186. As indicated in FIGS. 4 and 5, tubing system 186 may include a pair of one-way valves 186a, 186b to effect a first flow $f_2$ during upstroke of piston 162 and a second flow $f_1$ during downstroke of piston 162.

During ambulatory motion, a user shifts their weight from support by a heel portion 150 of the foot member, as shown in FIG. 4, toward support by toe portion 146 of the foot member, as shown in FIG. 5. Accordingly, as noted by comparing FIGS. 4 and 5, toe portion 146 flexibly rotates relative to shin member 114, as indicated by arrow P. The flexible rotation of the toe portion relative to the shin member causes piston 162 to reciprocate within pump chamber 160 as shown in FIGS. 4 and 5. This, in turn, draws fluid through tube system 186 as described above.

Pump 118 may also include a pressure regulator 178 to regulate the maximum negative pressure drawn within the socket-forming member 112. The regulator may be adjustable to select the maximum negative pressure within the system to levels which are safe and effective, as discussed with respect to the embodiment in FIGS. 1–3.

FIGS. 6–7 show another embodiment of a lower extremity prosthetic device suitable for use by an individual with a below the knee amputation, indicated generally at 210. Prosthetic device 210 may include a leg member 211, a foot member 216, and a pump 218. The leg member 211 may include a socket-forming member 212, a shin member 214, and an upper ankle 240. The socket-forming member may be provided with a port 226, which may be adapted to draw fluid (e.g., air) from within the socket-forming member so as to create or maintain a negative pressure therewithin, as discussed with respect to the embodiment shown in FIGS. 1–3.

Foot member 216 may be attached to leg member 211. In FIGS. 6–7, foot member 216 includes a lower ankle 242, a midfoot 244, and a toe plate 246. The lower ankle includes a heel 250, above which a resilient element 248 may be mounted as shown. Another resilient element 252 may also be provided.

In the embodiment shown in FIGS. 6–7, foot member 216 is pivotally movable relative to leg member 211. Specifically, lower ankle 242 is pivotally connected to upper ankle 240 by pivot member 254. The pivot member permits foot member to be pivotally rotated relative to the upper ankle, as indicated by arrow P. Because upper ankle 240 is fixed relative to shin member 214 and socket-forming member 212, the lower ankle is also pivotally rotatable relative to the shin member and the socket-forming member. The leg member and foot member of the embodiment shown in FIGS. 6–7 operate and interact in substantially the same manner as the embodiment shown in FIGS. 1–3.

Referring again to the embodiment in FIGS. 6–7, an integrated pump system 218 may be attached to leg member 211 above foot member 216. The pump includes a tether 270 attached to the foot member. Upon ambulatory motion, the foot member pivotally rotates relative to both the leg member and the pump. The foot member thereby acts upon the tether to actuate the pump, which draws negative pressure within the socket-forming member 212.

In the embodiment of FIGS. 6–7, integrated pump 218 may include a pump cylinder 260 which carries a reciprocating piston 262. A piston arm 266 is attached to the piston and reciprocates with the piston. Although not particularly shown, the piston may be urged to a neutral position within the cylinder by a spring or other bias mechanism. This neutral position may be selected in order to maximize the amount of negative pressure drawn by the pump within the socket-forming member during each iterative reciprocating motion of the piston. The tether 270, may be secured to piston arm 266, threaded through an eyelet in resilient element 248 and fixed to foot member 216. The tether thus links the piston and piston arm to the foot member such that the piston reciprocates as lower ankle 242 pivotally rotates relative to the upper ankle 240 during normal ambulatory motion of the user. The pump and foot member interact in substantially the same manner as the embodiment shown in FIGS. 1–3.

When foot member 216 is in a neutral position, as shown in FIGS. 6–7, piston 262 may also be positioned in a neutral position. FIGS. 6–7 illustrate the piston's neutral position to be near the top of cylinder 260. The neutral position of piston 262 within cylinder 260 may be adjustable similarly to the embodiment shown in FIGS. 1–3. As discussed in detail above, adjusting the position of the integrated pump 218 relative to the leg member 211 and foot member 216 may increase or decrease the amount of negative pressure drawn within the socket-forming member 212 with each stride of the user. Set screws 269 may be provided to loosen/tighten the attachment member 267 so as to adjust the position of the pump relative to the leg member. Further, reference portion 268 may be provided on piston arm 266 to provide a reference point for users to use when adjusting the position of the pump relative to the leg member and foot member. The reference portion thus enables a user to determine the optimal neutral position of the piston.

Integrated pump 218 may further include exhaust holes 285, which may cause exhaust liquid to flow out of the pump and away from prosthetic device 210. Unidirectional valves (not shown) may be provided within the integrated pump to ensure that exhaust liquids flow out of the pump through the exhaust holes, without flowing back into the socket-forming member 212, during an upstroke of piston 262. The unidirectional valves may also ensure that the downward reciprocating motion of the piston creates or maintain negative pressure within the socket-forming member 212.

Integrated pump 218 may further include an integrated regulator (not shown). As discussed in detail above, the regulator may serve to regulate the negative pressure established by the pump within socket-forming member 212. The regulator may further be adjustable by manipulating adjustment mechanism 272. A physician or health care professional thus may adjust the maximum negative pressure within the socket-forming member by adjusting the regulator to accommodate particular user needs. The desired maximum negative pressure for the prosthetic device shown in FIGS. 6–7 may be between 1–28 inches of mercury below ambient pressure. Further, the maximum negative pressure may be selected to ensure that the prosthetic device 210 is adequately secured onto the residual limb without causing detrimental physical effects to the user via excessive negative pressure.

Figure 9:
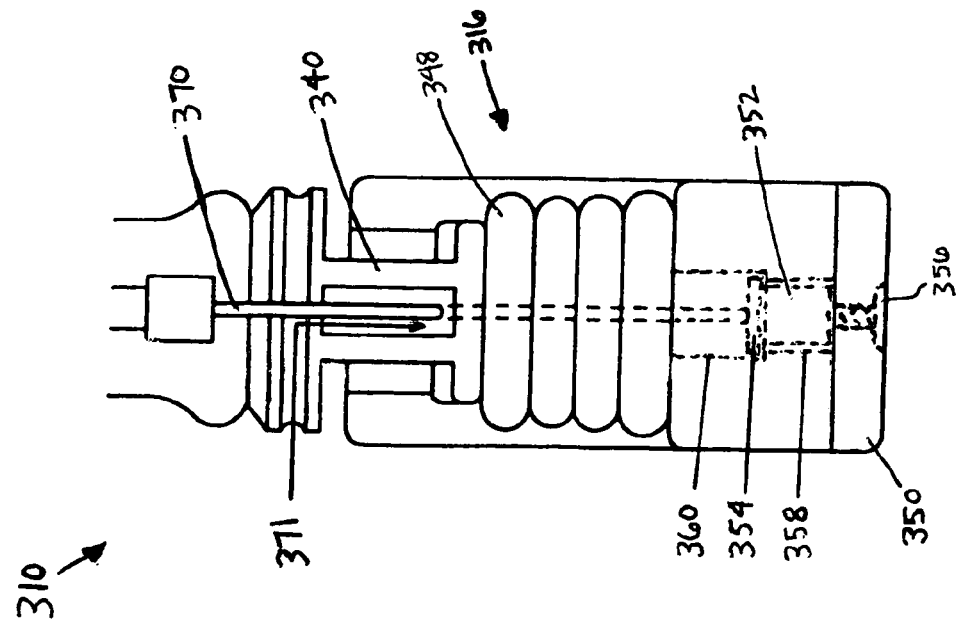
FIG. 9 is a rear view of the foot member of the prosthetic device shown in FIG. 8.
Figure 8:
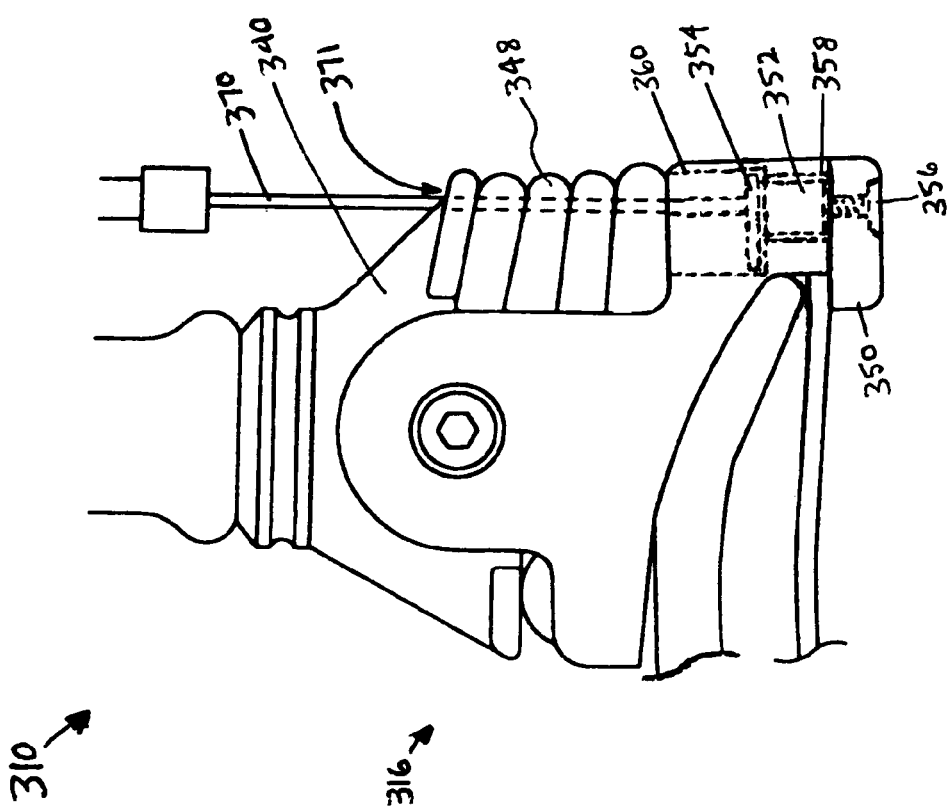
FIG. 8 is a side view of the foot member of a prosthetic device, according to yet another embodiment of the present invention.

FIGS. 8–9 show the foot member 316 of yet another embodiment of a lower extremity prosthetic device 310 suitable for use by an individual with a below the knee amputation. In particular, FIGS. 8–9 show an embodiment of a mechanism for attaching an actuator 370 to foot member 316. The actuator may be threaded through hole 371 in upper ankle 340 and resilient element 348. Actuator 370 may be attached by an anchor 352 to heel plate 350 using a bolt 356. The anchor may include an eccentric top 354, as is best shown in FIG. 8. The anchor may further be inserted into lower sleeve 358, which may provide a snug fit, while the eccentric top may fit within upper sleeve 360. When bolt 356 is used to attach anchor 352 to heel plate 350, eccentric top 354 prevents the anchor from rotating within lower sleeve 358 by displacing the anchor's axis of rotation from its center.

While the present invention has been particularly shown and described with reference to the foregoing depicted embodiments, those skilled in the art will understand that many variations may be made therein without departing from the spirit and scope of the invention as defined in the following claims. The description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element or the equivalent thereof, such claims should be understood to include incorporation of one or more such elements, neither requiring nor excluding two or more such elements.

I claim:

1. A prosthetic device for attachment to a residual limb, the prosthetic device comprising:
    a socket-forming member configured to receive the residual limb;
    a first portion;
    a second portion operatively connected to the first portion and rotatably movable relative to the first portion; and
    a pump attached to the first portion and adapted to draw a negative pressure within the socket-forming member upon rotating movement of the second portion relative to the first portion, wherein the pump includes an actuator operatively associated with the second portion such that the second portion acts on the actuator to effect drawing of the negative pressure by the pump upon selected rotational movement of the second portion relative to the first portion.

2. The prosthetic device of claim 1, wherein the first portion is pivotal rotatable relative to the second portion.

3. The prosthetic device of claim 1, wherein the first portion is flexible relative to the second portion.

4. The prosthetic device of claim 1, wherein the actuator is a tether fixedly connected to the second portion.

5. The prosthetic device of claim 4, wherein the tether is at least one of a cable, a strap, a cord, a wire, a string, or a rod.

6. The prosthetic device of claim 1, wherein the position of the pump relative to the second portion affects the amount of negative pressure drawn by the pump with each iterative rotational movement of the first portion relative to the second portion.

7. The prosthetic device of claim 6, wherein the position of the pump relative to the first portion is adjustable to selectively alter the position of the pump relative to the second portion.

8. The prosthetic device of claim 1, wherein the pump further includes an exhaust system configured to expel fluids drawn from the socket-foming member.

9. The prosthetic device of claim 1, wherein the pump further includes a regulator configured to control a maximum negative pressure drawn within the socket-forming member.

10. The prosthetic device of claim 9, wherein the regulator includes an adjustment mechanism configured to adjust the maximum negative pressure the regulator permits to be drawn within the socket-forming member.

11. The prosthetic device of claim 10 wherein the regulator is configured to permit the pump to maintain maximum negative pressures between 1 and 28 inches of mercury within the socket-forming cavity.

12. A prosthetic device for attachment to a residual limb, the prosthetic device comprising:
    a leg member including a socket-forming member configured to receive the residual limb;
    a foot member pivotally connected to the leg member; and
    a pump mounted on the leg member and including an actuator operatively connected to the foot member, the pump being adapted to draw a negative pressure within the socket-forming member upon pivot of the foot member relative to the leg member during ambulatory motion, wherein the actuator is a tether operatively connecting the pump to the foot member.

13. The prosthetic device of claim 12, wherein the tether is attached to an anchor with an eccentric top, and the anchor is attached to the foot member with a bolt.

14. The prosthetic device of claim 12, wherein the tether is at least one of a cable, a cord, a wire, a string, or a rod.

15. The prosthetic device of claim 12, wherein position of the pump relative to the foot member affects an amount of negative pressure drawn by the pump with each iterative pivot of the foot member relative to the leg member during ambulatory motion.

16. The prosthetic device of claim 15, wherein an attachment position of the pump on the leg member is adjustable to selectively alter the position of the pump relative to the foot member.

17. The prosthetic device of claim 16, wherein the pump further includes a reference portion configured to facilitate adjustment of the attachment position of the pump.

18. The prosthetic device of claim 12, wherein the pump further includes an exhaust configured to expel fluids drawn from the socket-forming member.

19. The prosthetic device of claim 12, wherein the pump further includes a regulator configured to control a maximum negative pressure drawn within the socket-foming member.

20. The prosthetic device of claim 19, wherein the regulator includes an adjustment mechanism configured to adjust the maximum negative pressure the regulator permits to be drawn within the socket-forming member.

21. The prosthetic device of claim 20 wherein the regulator is configured to permit the pump to maintain maximum negative pressures between 1 and 28 inches of mercury within the socket-forming cavity.

22. A prosthetic device for attachment to a residual limb, the prosthetic device comprising:
 a leg member including a socket-forming member configured to receive the residual limb;
 a foot member connected to the leg member and flexible relative to the leg member; and
 a pump mounted an the leg member and including an actuator operatively connected to the foot member, the pump being adapted to draw a negative pressure within the socket-forming member upon flexure of the foot member during ambulatory motion, wherein the actuator is a tether attached to the foot member.

23. The prosthetic device of claim 22, wherein the tether is at least one of a cable, a cord, a wire, a string, or a rod.

24. The prosthetic device of claim 22, wherein position of the pump relative to the foot member affects an amount of negative pressure drawn by the pump with each iterative flexure of the foot member relative to the leg member during ambulatory motion.

25. The prosthetic device of claim 24, wherein an attachment position of the pump on the leg member is adjustable to selectively alter the position of the pump relative to the foot member.

26. The prosthetic device of claim 25, wherein the pump further includes a reference portion configured to facilitate adjustment of the attachment position of the pump.

27. The prosthetic device of claim 22, wherein the pump further includes an exhaust configured to expel fluids drawn from the socket-foming member.

28. The prosthetic device of claim 22, wherein the pump further includes a regulator configured to control a maximum negative pressure drawn within the socket-forming member.

29. The prosthetic device of claim 28, wherein the regulator includes an adjustment mechanism configured to adjust the maximum negative pressure the regulator permits to be drawn within the socket-forming member.

30. The prosthetic device of claim 29 wherein the regulator is configured to permit the pump to maintain maximum negative pressures between 1 and 28 inches of mercury within the socket-forming cavity.

31. A prosthetic device for attachment to a residual limb the prosthetic device comprising:
 a leg member including a socket-forming member configured to receive the residual limb;
 a foot member pivotally connected to the leg member; and
 a pump mounted on the leg member and adapted to draw a negative pressure within the socket-forming member upon pivot of the foot member relative to the leg member during ambulatory motion, the pump including:
 a tether attached to the foot member;
 an exhaust system configured to expel fluids drawn from the socket-forming member; and
 a regulator configured to control the maximum negative pressure drawn within the socket-forming member.

32. A prosthetic device for attachment to a residual limb, the prosthetic device comprising:
 a leg member including a socket-forming member configured to receive the residual limb;
 a foot member connected to the leg member and flexibly rotatable relative to the leg member; and
 a pump mounted on the leg member and adapted to draw a negative pressure within the socket-forming member when the foot member flexibly rotates relative to the leg member during ambulatory motion, the pump including:
 a tether attached to the foot member;
 an exhaust system configured to expel fluids drawn from the socket-forming member; and
 a regulator configured to control the maximum negative pressure drawn within the socket-forming member.

* * * * *